United States Patent [19]
Rössling et al.

[11] Patent Number: 5,501,863
[45] Date of Patent: Mar. 26, 1996

[54] CONTRAST MEDIA SYNTHESIZED FROM POLYALDEHYDES

[75] Inventors: Georg Rössling; Celal Albayrak; Matthias Rothe; Joachim Siegert, all of Berlin, Germany

[73] Assignee: Schering Aktiengesellschaft, Berlin, Germany

[21] Appl. No.: 373,467

[22] Filed: Jan. 17, 1995

Related U.S. Application Data

[63] Continuation of Ser. No. 95,500, Jul. 26, 1993, abandoned, which is a continuation of Ser. No. 653,792, Feb. 11, 1991, abandoned.

[30] Foreign Application Priority Data

Feb. 9, 1990 [DE] Germany .......................... 40 04 430.0

[51] Int. Cl.⁶ .............................. A61K 9/50; A61K 49/00
[52] U.S. Cl. .......................... 424/489; 424/490; 424/495; 424/501; 428/402.2; 428/402.21; 428/403; 128/660.01
[58] Field of Search .................... 424/489, 490, 424/497, 501; 428/402.2, 402.21, 403; 128/660.01

[56] References Cited

U.S. PATENT DOCUMENTS

| | | | |
|---|---|---|---|
| 4,267,234 | 5/1981 | Rembaum | 428/403 |
| 4,276,885 | 7/1981 | Tickner | 424/9 |
| 4,349,530 | 9/1982 | Royer | 424/489 |
| 4,438,239 | 3/1984 | Rembaum et al. | 522/175 |
| 4,677,138 | 6/1987 | Margel | 424/489 |
| 4,678,814 | 7/1987 | Rembaum et al. | 522/175 |
| 4,718,433 | 1/1988 | Feinstein | 530/427 |
| 4,732,811 | 3/1988 | Margel | 428/403 |
| 4,783,336 | 11/1988 | Margel et al. | 424/489 |
| 4,937,081 | 6/1990 | Kagotani | 424/489 |
| 4,997,454 | 3/1991 | Violante | 424/489 |
| 5,019,400 | 5/1991 | Gomobotz | 424/489 |

FOREIGN PATENT DOCUMENTS

| | | |
|---|---|---|
| 0324938 | 7/1989 | European Pat. Off. |
| 06978 | 8/1989 | WIPO. |

*Primary Examiner*—Raj Bawa
*Attorney, Agent, or Firm*—Millen, White, Zelano, & Branigan

[57] ABSTRACT

Microparticles comprising biodegradable polymers, characterized in that they are synthesized from polymerizable aldehydes, which optionally contain additives and/or crosslinkers capable of copolymerization, optionally surfactants or surfactant mixtures, gases and/or highly volatile liquids in free or bound form, coupling agents, optionally biomolecules or macromolecules bound by these coupling agents as well as optionally diagnostically or therapeutically effective components, are suitable as ultrasonic contrast media.

25 Claims, 4 Drawing Sheets

CONTRAST MEDIA SYNTHESIZED FROM POLYALDEHYDES

This application is a continuation of application Ser. No. 08/095,500, filed Jul. 26, 1993, now abandoned, which is a continuation of application Ser. No. 07/653,792, filed Feb. 11, 1991, now abandoned.

BACKGROUND OF THE INVENTION

The invention relates to new microparticles, pharmaceutical agents containing them, their use, e.g., in ultrasonic diagnosis as well as processes for the production of these microparticles and pharmaceutical agents.

It is known that by peripheral injection of solutions, which contain fine gas bubbles, cardiac echo contrasts can be achieved (Roelandt J., Ultrasound Med. Biol. 8: 471–492, 1982). These air bubbles are obtained in physiologically compatible solutions, e.g., by shaking, other agitation or by addition of carbon dioxide. But they are not uniform in regard to number and size and can be reproduced only unsatisfactorily. Also they generally are not stabilized so that their life is short. Their average diameters in most cases are above the size of erythrocytes so that no lung capillary passage with subsequent contrasting of organs such as left heart, liver, kidney or spleen is possible. Further, they are not suitable for quantifications, since the ultrasound echo produced by them is composed of several inseparable processes such as bubble formation, coalescence and dissolution. Thus, e.g., it is not possible with these ultrasonic contrast media to obtain displays on transit times by the measurement of the contrast course in the myocardium.

The stabilization of the gas bubbles by sugar is described in EP 0 131 540. Thus the reproducibility and homogeneity of the contrast effect is indeed improved but these bubbles do not survive a lung passage.

It is described in EP 0 122 624 and 0 123 235 that the gas bubble stabilizing effect of sugars, sugar alcohols and salts is improved by addition of surfactants. A lung capillary passage and the possibility of representation of the arterial vessel branch and different organs such as liver and spleen exists with this ultrasonic contrast media. But here the contrast effect is limited to the vessel lumen, since the bubbles are not absorbed by the tissue cells.

None of the ultrasonic contrast media known so far remains unchanged for a prolonged period in the body. Therefore an organ representation with sufficient signal intensity by selective concentration after i.v. injection or quantifications are not possible.

An encapsulation of gases, such as, for example, air as ultrasonic contrast media, is described in DE-OS 38 03 972. The wall material used here consists of biodegradable synthetic material, such as especially cyanoacrylate and polylactide.

But these microparticles—especially on larger scale as well as in regard to their working up—are difficult to produce. Thus especially the broad size distribution of these particles is a drawback.

SUMMARY OF THE INVENTION

This invention provides ultrasonic contrast media, which do not exhibit these drawbacks and is achieved by the provision of the microparticles according to the invention.

These microparticles consist of biodegradable polymers, characterized in that they are synthesized from polymerizable aldehydes, which optionally contain additives and/or crosslinkers capable of copolymerization, optionally surfactants or surfactant mixtures, gases and/or highly volatile liquids in free or bound form, coupling agents, optionally biomolecules or macromolecules bound by these coupling agents as well as optionally diagnostically or therapeutically effective components.

In general, the polymerizable aldehydes can be selected from a wide variety of R-CHO groups, wherein R is non-critical and can be selected from, e.g., $C_{1-10}$ hydrocarbons which can be saturated or unsaturated, acyclic or cyclic, aliphatic or aromatic, optionally substituted by halo, other such hydrocarbon groups, CN, CHO, etc. Preferred are alkane aldehydes, acrolein derivatives and dialdehydes.

Suitable polymerized aldehydes useful in the synthesis of the microparticles can be selected from the following exemplary preferred polymerizable aldehyde monomers:

I. alpha,beta-unsaturated aldehydes, such as, for example
   acrolein
   crotonaldehyde
   propynoicaldehyde II. alpha-substituted acrolein derivatives, such as, for example
   alpha-methyl acrolein
   alpha-chloroacrolein
   alpha-phenyl acrolein
   alpha-ethyl acrolein
   alpha-isopropyl acrolein
   alpha-n-butyl acrolein
   alpha-n-propyl acrolein III. Dialdehydes, such as, for example
   glutaraldehyde, succinaldehyde or their derivatives or their mixtures with additives capable of copolymerization (comonomers), such as, for example
   alpha-substituted acroleins
   beta-substituted acroleins
   ethyl cyanoacrylates
   methyl cyanoacrylates
   butyl cyanoacrylates
   hexyl cyanoacrylates
   methyl methacrylates
   vinyl alcohols
   acrylic acids
   methacrylic acids
   acrylic acid chlorides
   methacrylic acid chlorides
   acrylonitrile
   methacrylonitriles
   acrylamides
   substituted acrylamides
   hydroxy methyl methacrylates
   mesityl oxide
   dimethylaminoethylmethacrylates 2-vinylpyridines
   N-vinyl-2-pyrrolidinone In this case, acrolein and glutaraldehyde are preferred. Comonomers of any of the foregoing aldehydes with each other and with the other comonomers mentioned above are also included. In general, the amount of aldehyde monomer in the copolymers is 50–100 mole %, preferably 75–100 mole %, the remainder being the non-aldehyde. Where all comonomers are aldehydes, the relative amounts are not critical, e.g., any can be present in an amount of 0–100 mole %.

All polymers (homopolyaldehydes or copolyaldehydes) of this invention typically have molecular weights of 1,000 d to 30,000 d, preferably 1,000 d to 12,000 d. The particles are biodegradable in blood and plasma.

The surfactants optionally involved in the synthesis of the microparticles can be selected non-critically from ionic (cationic or anionic) or nonionic surface-active substances (surfactants), such as, e.g.

polyethylene oxide
polyoxyethylene polyoxypropylenes such as
Pluronic$^{(R)}$ F 68, Pluronic$^{(R)}$ F 108, Pluronic$^{(R)}$ F 127, polyethylene glycol, Poloxamin 908, Polaxamer 407
carboxylic acid salts, such as, for example, sodium oleate
polyoxyethylene fatty acid esters, such as, for example:
polyoxyethylene stearate
sodium dioctyl sulfosuccinate
polyglutaraldehyde sodium hydrogensulfite adduct
polyacrolein sodium hydrogensulfite adduct
polyvinyl sulfonic acid.

They can be used alone or in the form of their mixtures, the relative amounts being non-critical.

Preferred of these are: polyglutaraldehyde sodium sulfite adduct, polyacrolein sodium hydrogensulfite adduct, Pluronic$^{(R)}$ F68, Pluronic$^{(R)}$ F 108 and Pluronic$^{(R)}$ F 127.

If the polymerizable aldehydes used for the synthesis of the microparticles themselves have surfactant properties, then surfactants may not be used, but also can be used. As an example of such aldehydes, glutaraldehyde can be mentioned. Typically, the amount of surfactant relative to the amount of polyaldehyde is 0.01–1 wt. % and preferred surface tension values for the surfactants are 40–50 mN/m.

As gases or highly volatile liquids contained in the microparticles in free or bound form—in this case, liquids with a boiling point below 60° C. are preferred—e.g., there are suitable physiologically acceptable ones (at the minor amounts used) such as:

ammonia
air
inert gases (helium, neon, argon, xenon, krypton)
sulfur halides, such as, for example: sulfur hexafluoride
nitrogen
carbon oxides
oxygen
hydrogen Hydrocarbons or their mixtures, such as, for example:
methane
ethane
propane
butane
pentane
neopentane
isopentane
cyclopentane
ethylene
propylene
acetylene
3,3-dimethyl-1-butyne
2,3-pentadiene
2-methyl-2-butene
2-methyl-1,3-butadiene
2-butyne
2-methyl-1-butene
3-methyl-1-butene halogenated hydrocarbons or mixtures, such as, for example:
methylene chloride
1,1-dichloroethylene
isopropyl chloride
dibromodifluoromethane
bromomethane
ethers, such as, for example: dimethyl ether, diethyl ether or fluorinated ethers,
or compounds such as, for example:
dimethylaminoacetone
propylene oxide
N-ethylmethylamine
N-ethyldimethylamine
furan Of these, air, argon, xenon, sulfur hexafluoride, propane, butane and furan are preferred.

By "free" in this context is meant that the gas or volatile liquid is contained in the microparticle by physical trapping whereas by "bound" is meant a trapping by weak chemical bonding short of covalent bonding. Typical amounts relative to the amount of polymers are 0.01–2 wt. % for both the gases and volatile liquids.

As coupling agents utilizable in the synthesis of the microparticles there are especially suitable:

I. Compounds containing amino groups, such as, for example:
hydroxylamine
butylamine
allylamine
ethanolamine
trishydroxymethylaminomethane
3-amino-1-propanesulfonic acid
5-aminovaleric acid
8-aminooctanoic acid
D-glucosamine hydrochloride
aminogalactose
aminosorbitol
aminomannitol
diethylaminoethylamine
anilines
sulfonyl acid amide
choline
N-methylglucamine
piperazine
1,6-hexanediamine
urea
hydrazine
glycine
alanine
lysine
serine
valine
leucine
peptides proteins
albumin
human serum albumin
polylysine
gelatin
polyglycolamines
aminopolyalcohols
dextran sulfates with amino groups
N-aminopolyethylene glycol (HO-PEG-NH$_2$)
N,N'-diaminopolyethylene glycol ( NH$_2$-PEG-NH$_2$ )
antibodies
immunoglobulins II. Compounds containing acid groups, such as, carboxylic acids
  acetic acid
  propionic acid
  butyric acid
  valeric acid
  caproic acid
  caprylic acid
  capric acid
  lauric acid
  myristic acid
  palmitic acid
  stearic acid
  oleic acid
  linolic acid
  linolenic acid
  cyclohexane carboxylic acid
  phenylacetic acid
  benzoylacetic acid
  chlorobenzoic acid
  bromobenzoic acid
  nitrobenzoic acid
  ortho-phthalic acid
  meta-phthalic acid
  para-phthalic acid
  salicylic acid
  hydroxybenzoic acid
  aminobenzoic acid
  methoxybenzoic acid (PEG linker asparaginic acid)

PEG-linker-glutaminic acid
  PEG-linker-DTPA
  PEG-linker-EDTA

III. Compounds containing hydroxy groups, such as, for example: alcohols
  methanol
  ethanol
  propanol
  butanol
  pentanol
  hexanol
  heptanol
  octanol
  decanol
  dodecanol
  tetradecanol
  hexadecanol
  octadecanol
  isopropyl alcohol
  isobutyl alcohol
  isopentyl alcohol
  cyclopentanol
  cyclohexanol
  crotyl alcohol
  benzyl alcohol
  phenyl alcohol
  diphenyl methanol
  triphenyl methanol
  cinnamyl alcohol
  ethylene glygol
  1,3-propanediol
  glycerol
  pentaerythritol IV. Polymerizable substances, such as alpha,beta-unsaturated aldehydes, such as, e.g.:
  acrolein
  crotonaldehyde
  propionaldehyde
  alpha-substituted acrolein derivatives, such as, e.g.:
  alpha-methylacrolein
  alpha-chloroacrolein
  alpha-phenylacrolein
  alpha-ethylacrolein
  alpha-isopropylacrolein
  alpha-n-butylacrolein
  alpha-n-propylacrolein
  dialdehydes, such as, e.g.:
  glutaraldehyde, succinaldehyde or their derivatives or their mixtures with additives capable of copolymerization, such as, e.g.:
  alpha-substituted acroleins
  beta-substituted acroleins
  ethyl cyanoacrylates
  methyl cyanoacrylates
  butyl acrylates
  hexyl cyanoacrylates
  methylmethacrylates
  vinyl alcohols
  acrylic acids
  methacrylic acids
  acrylic acid chlorides
  acrylonitrile
  methacrylonitriles
  acrylamides
  substituted acrylamides
  hydroxymethylmethacrylates
  mesityl oxide
  dimethylaminoethylmethacrylates 2-vinylpyridines
  N-vinyl-2-pyrrolidinone Of these there are preferred: hydroxylamine, trishydroxymethylaminomethane, 3-amino-1-propane sulfonic acid, D-glucosaminohydrochloride, aminomannitol, urea, human serum albumin, hydrazine, proteins, polyglycolamines, aminopolyalcohols such as, e.g., HO-PEG-NH$_2$ or NH2-PEG-NH$_2$ or compounds containing acid groups such as, e.g., PEG-linker-asparaginic acid, PEG-linker-glutaminic acid, PEG-linker-DTPA and PEG-linker-EDTA, and the molecular weight of the polyethyleneglycol (PEG) is up to 100,000 d, preferably under 40,000 d. The amount of coupling agent is typically, based on the amount of polyaldehyde, 1–95 wt. %.

The coupling agents named under I can be condensed by their amino group on the formyl groups located on the surface of microparticles synthesized from polymerized aldehydes and optionally surfactants.

Also the monomers listed under IV, which can be polymerized with other monomers, can be bound by the formyl groups.

On the other hand, the acids and alcohols named under II and III are typically coupled on the microparticles only after previous conventional conversion of the aldehyde function, e.g., as discussed below.

By the selection of suitable biomolecules or macromolecules, bound by these coupling agents, such as, e.g., enzymes, dextrans, immunoglobulins, monoclonal antibodies (see below), microparticles according to the invention are obtained, which exhibit a surprisingly high tissue and organ specificity.

The microparticles according to the invention optionally can contain diagnostically or therapeutically effective components for diagnosis and therapy of tumors, such as, for example doxorubicin
actinomycin
magnetite
mitomycin C
triamcinolone, among many others, typically in amounts up to 90 wt. % based on the amount of polyaldehyde, precise amounts being routinely determinable in accordance with typical dosages for the active agent and other conventional considerations.

The microparticles of the present invention are surprisingly better compatible especially in view of cardiovascular effects (blood pressure, heart-arrhythmia) and the particles show no thrombogenic potential.

The microparticles according to the invention exhibit the described desired properties. They can be produced simply and with high yield. An upscaling of their production, as well as their purification, is no problem.

As crosslinkers useful in this invention are included the components listed below as bifunctional linkers; typical amounts are 0–5 wt. %. Comonomers and crosslinkers are typically included to enhance the stability of the microparticles.

The particles exhibit a narrow size distribution (monodisperse); at the same time, it is possible to vary the size of the particles over a wide range depending on the concentration of the starting materials used (see below). By control of the production conditions (e.g., pH) it is possible also to vary the molecular weight in wide ranges. Shapes are not critical and typically are sphere-like.

Another advantage consists in the fact that the reaction for the synthesis of the microparticles can be brought about by many possibilities known in principle for polymerization of aldehydes, for example, anionic polymerization by change of pH, cationic polymerization, e.g., with iron salts, radical polymerization with UV light and by ionizing radiation.

The broad temperature range (–5° to +80° C.), possible for the production of the microparticles, allows a simple experimental control with optimal yields with very different gases or low-boiling liquids.

The particles contain free aldehyde groups, which can be covalently linked to other molecules by chemical reactions, e.g., as described above for coupling agents. This possibility allows the properties of the particle surface to be deliberately changed without affecting the echogenic properties. The colloidal stability can be affected by the selection of suitable molecules as coupling agents. Especially in this way the phenomenon of agglomeration often occurring for colloidal systems can be prevented. This again is a great advantage for the development of a stable formulation.

Besides affecting the stability, possibilities are offered of changing the surface of the particles so that a drug targeting is possible. This occurs by coupling on of suitable biomolecules or macromolecules (e.g., monoclonal antibodies), which cause a high tissue and organ specificity (G. Gregoriadis, G. Poste, "Targeting of Drugs," Plenum Press 1988 New York) or by affecting the surface properties of the particles by absorption of molecules (e.g., surfactants).

As a function of the selection of these molecules and of the size of the microparticles, a particle concentration can be achieved in/on tumors or, e.g., in the lung, liver, spleen and in the bone marrow. The concentration in the bone marrow is especially achieved in that small particles (less than 100 nm) are coated, e.g., with Poloxamer 407. If these particles, e.g., are coated with Poloxamin 908, the RES is overcome by these particles, and they remain in the blood circulation (blood pool agent). Typical coating thicknesses are up to 2 nm.

By particles coupled with antibodies, a concentration of the particles in/on tumors can be achieved.

An active targeting can also be performed with microparticles containing magnetite. The particles are concentrated in the desired places in the intravasal system by an externally applied magnetic field. The possibility to investigate circulatory conditions, e.g., in the blood vessels, is thus achieved.

With the help of particles laden with magnetite it is also possible to produce locally high temperatures by an externally irradiated alternating magnetic field. This can be used therapeutically, e.g., for the destruction of tumors (hyperthermy therapy). ("Hyperthermia", Overgaard, J., The current and potential role of hyperthermia in radiotherapy. Int. J. Radiat. Oncol. Biol. Phys. 1989, 16:535–549.) An ultrasonic field can also be used, besides the use of a magnetic alternating field. As a result, at the same time strong local temperature increases also occur. (WO 89/05160—use of media containing bubbles in shockwave and ultrasonic therapy.)

The production of the microparticles according to the invention can take place in that with stirring an aqueous solution containing 0 to 40%, preferably 0.01 to 10% w/v of surfactant(s) and 0 to 10% w/v of diagnostically or therapeutically effective components and gases or highly volatile liquids, at a temperature of –5° C. to +80° C., preferably 0° C. to 40° C., a pH of 7 to 14, preferably 9 to 13, within 1 minute to 24 hours, preferably 1 hour to 10 hours, and optionally with the passage of gas therethrough, is reacted with copolymerizable aldehyde(s) up to a concentration relative to the reaction mixture of 0.1 to 50%, preferably 3 to 20% w/v, as well as with copolymerizable additives of a concentration relative to the reaction solution of 0 to 20%, preferably 1 to 5% w/v, with crosslinker(s) of a concentration relative to the reaction mixture of 0–5%, preferably 0.1 to 1% w/v, then— optionally after purification—the microparticles thus obtained are reacted with an aqueous solution, which contains—relative to the aldehyde group content of the microparticles—up to equimolar amounts of coupling agent as well as 0 to 20%, preferably 0.01 to 10% w/v surfactant(s) relative to the total volume, with stirring up to 3 days, preferably up to 2 days, at temperatures of 0° C. to 60° C., preferably 5° C. to 30° C., at a pH of 3 to 9, preferably 5 to 8, and—optionally after purification—these optionally are bound to biomolecules or macromolecules.

The polymer aldehyde particles, obtained after the first reaction step, have aldehyde groups on the surface. With these aldehyde groups the reactions typical for aldehydes can be performed (R. C. Schulz, Kolloidzeitschrift und Zeitschrift fuer Polymere, 182 (1–2), 99 (1961); Lehrbuch der organischen Chemie [Textbook of Organic Chemistry] "Organikum," VEB Verlag der Wissenschaften, Berlin, 1984). Thus, it is possible to couple molecules on the particle surface which change the surface properties.

Examples for possible reactions of the aldehyde groups:
reduction to alcohol
oxidation to acids
oximation
imine formation, optionally followed by hydrogenation and optionally then N-alkylation
hydrazone formation, optionally followed by hydrogenation
mercaptalization
acetalation
disproportionation by NaOH (Cannizzaro reaction)
aldol condensation.

The coupling of molecules containing amino groups on the particles formed in the first reaction step takes place by reaction with the aldehyde groups. In this case, for example, the following exemplary experimental conditions can be used;

1000 mg of polyacrolein particles are suspended in 50 ml of distilled water. 5000 mg of the substance to be reacted is added to this particle suspension and stirred at room temperature. Stirring is accomplished in keeping with the reaction rate of the reaction; at slow reaction rates up to 48 hours. The particle suspension is then dialyzed (cut off 10000 d).

If the substituents introduced, e.g., by the above-indicated reactions, contain (optionally intermediately protected) functional groups, the latter can be converted according to processes known to one skilled in the art into reactive groups suitable for coupling to biomolecules or macromolecules. Preferred such groups are, for example, the maleimidobenzoyl, 3-sulfomaleimidobenzoyl, 4-(maleimidomethyl)-cyclohexylcarbonyl, 4-[ 3-sulfo-(maleimido-methyl)-cyclohexyl-carbonyl, 4-(p-maleimidophenyl)-butyryl, 3-(2-pyridyl-dithio)propionyl), methacryloyl-(pentamethylene)-amido, bromoacetyl, iodoacetyl, 3-iodopropyl, 2-bromoethyl, 3-mercaptopropyl, 2-mercaptoethyl, phenyleneisothiocyanate, 3-aminopropyl, benzyl ester, ethyl ester, t-butyl ester, amino, $C_1$–$C_6$ alkylamino, aminocarbonyl, hydrazino, hydrazinocarbonyl, maleimido, methacrylamido, methacryloylhdrazinocarbonyl, maleimidamidocarbonyl, halo, mercapto, hydrazinotrimethylenehydrazinocarbonyl, aminodimethyleneamido, carbonyl, bromocarbonyl, phenylenediazonium, isothiocyanate, semicarbazide, thiosemicarbazide, isocyanate groups.

An amino group can, for example, be converted into an isothiocyanate group according to methods known in the literature (e.g., with thiophosgene in a two-phase system, S. Scharma, Synthesis 1978, 803, D. K. Johnson, J. Med. Chem. 1989, Vol. 32, 236).

By the reaction of an amino function an alpha-haloacetamide group can be generated with a haloacetic acid halide (JACS 1969, Vol. 90, 4508; Chem. Pharm. Bull. 29 (1), 128, 1981), which, just as, e.g., the isothiocyanate group, is suitable for coupling to biomolecules or macromolecules.

As substituent, which can be converted into a functional group suitable for binding to a macromolecule or biomolecule, suitable among others are hydroxy and nitrobenzyl, hydroxy and carboxy alkyl as well as thioalkyl radicals with up to 20 carbon atoms. They are converted according to processes known in the literature to one skilled in the art [Chem. Pharm. Bull. 33, 674 (1985), Compendium of Org. Synthesis Vol. 1–5, Wiley and Sons, Inc., Houben-Weyl, Methoden der organischen Chemie [Methods of Organic Chemistry], Vol. VIII, Georg Thieme Verlag, Stuttgart, J. Biochem. 92,1413, (1982)] into the desired substituents (for example, with amino, hydrazino, hydrazinocarbonyl, epoxide, anhydride, methacryloylhdrazinocarbonyl, maleimidamidocarbonyl, halo, halocarbonyl, mercapto, isothiiocyanate group as functional group), and in the case of the nitrobenzyl radical first a catalytic hydrogenation (for example, according to P. N. Rylander, Catalytic Hydrogenation over Platinum Metals, Academic Press 1967) to the aminobenzyl derivative can be performed.

Examples for the conversion of hydroxy or amino groups, bound on aromatic or aliphatic radicals, are the reactions performed in suitable solvents such as tetrahydrofuran, dimethoxyethane or dimethyl sulfoxide, two-phase aqueous systems, such as, e.g., water/dichloromethane, in the presence of an acid trap such as, for example, sodium hydroxide, sodium hydride or alkali or alkaline-earth carbonates such as, for example, sodium, magnesium, potassium, calcium carbonate or poly-(4-vinylpyridine) Reillex at temperatures between 0° C. and the boiling point of the respective solvent, but preferably between 20° C. and 60° C. with a substrate of general formula I

$$Nf-L-Fu \qquad (I),$$

in which Nf is a nucleofuge such as, e.g., Cl, Br, I, $CH_3C_6SO_3$ or $CF_3SO_3$, L stands for an aliphatic, aromatic, arylaliphatic, branched, straight-chain or cyclic hydrocarbon radical with up to 20 carbon atoms and Fu stands for the desired functional group, optionally in protected form (DE-OS 34 17 413).

As examples for compounds of general formula I there can be mentioned

Conversions of carboxy groups can be performed, for example, according to the carbodiimide method (Fieser, Reagents for Organic Syntheses 10, 142), by a mixed anhydride [Org. Prep. Proc. Int. 7, 215 (1975) or by an activated ester (Adv. Org. Chem. Part B, 472).

The microparticles carrying coupling agents thus obtained can also be linked to biomolecules or macromolecules of which it is known that they especially concentrate in the organ or organ part to be examined. Such molecules are, for example, enzymes, hormones, polysaccharides such as dextrans or starches, porphyrins, bleomycins, insulin, prostaglandins, steroid hormones, amino sugars, amino acids, peptides such as polylysine, proteins (such as, for example, immunoglobulins, monoclonal antibodies), lectins, lipids (also in the form of liposomes) and nucleotides of DNA and RNA type. Especially to be emphasized are conjugates with albumins, such as human serum albumin, antibodies, such as, for example, monoclonal antibodies or antimyosin specific for tumor-associated antigens. Instead of biological macromolecules suitable synthetic polymers such as polyethylenimines, polamides, polyureas, polyethers such as polyethylene glycols and polythioureas can be linked on. The pharmaceutical agents formed from them are suitable, for example, for use in tumor and infarct diagnosis as well as tumor therapy. Monoclonal antibodies (for example, Nature 256, 495, 1975) in comparison with polyclonal antibodies have the advantages that they are specific for an antigenic determinant, have a defined binding affinity, are homogeneous (thus their pure representation becomes substantially simpler) and can be produced in cell cultures in large amounts. As such, for example, monoclonal antibodies or their fragments Fab and F(ab')$_2$ are suitable for tumor representation, which, for example, are specific for human tumors of the gastrointestinal tract, the breast, the liver, the bladder, the reproductive glands and of melanomas [Cancer Treatment Repts. 68, 317, (1984), Bio. Sci. 34, 150 (1984)] or are directed against carcinoembryonic antigen (CEA), human chorionic gonadotropin (beta-HCG) or other tumor-position antigens, such as glycoproteins [New Engl. J. Med. 298, 1384, (1973), U.S. Pat. No. 4,331,647]. Antimyosin, anti-insulin and antifibrin antibodies (U.S. Pat. No. 4,036,945) among others are also suitable.

Colon carcinomas can be diagnostically detected with microparticle conjugates with antibodies 17-1A (Centocor, USA).

In the case of the antibody conjugates the binding of the antibody on the microparticles must not lead to the loss or the reduction of the binding affinity and binding specificity of the antibody for the antigen. This can take place either by binding on the carbohydrate portion in the Fc part of the glycoprotein or in the Fab or F(ab')$_2$ fragments or by binding on sulfur atoms of the antibody or the antibody fragments.

In the first case, first an oxidative cleavage of sugar units for generation of formyl groups able to be coupled has to be performed. This oxidation can be performed chemically with oxidants such as, e.g., periodic acid, sodium metaperiodate or potassium metaperiodate according to methods known in the literature (for example, J. Histochem and Cytochem. 22, 1084, 1974) in aqueous solution in concentrations of 1 to 100, preferably 1 to 20 mg/ml, and a concentration of the oxidant between 0.001 to 10 mmol, preferably 1 to 10 mmol, in a pH range of about 4 to 8 at a temperature between 0° and 37° C. and a reaction period between 15 minutes and 24 hours. The oxidation can also be performed enzymatically, for example with galactoseoxidase, in an enzyme concentration of 10–100 units/ml, a substrate concentration of 1 to 20 mg/ml, at a pH of 5 to 8, a reaction period of 1 to 8 hours and a temperature between 20° and 40° C. (for example. J. Biol. Chem. 234, 445, 1959).

Microparticles with suitable functional groups, such as, for example, hydrazine, hydrazide, hydroxylamine, phenylhydrazine, semicarbazide and thiosemicarbazide, by reaction between 0° and 37° C., in a reaction period of 1 to 65 hours, a pH between about 5.5 and 8, an antibody concentration of 0.5 to 20 mg/ml and a molar ratio of complexing agent to antibody aldehydes of 1:1 to 1000:1 are bound on the aldehydes generated by oxidation. The subsequent stabilization of the conjugate takes place by reduction of the double bond, e.g., with sodium borohydride or sodium cyanoborohydride; in this case the reducing agent is used in 10- to 100-fold excess (for example, J. Biol. Chem. 254, 4359, 1979).

The second possibility of formation of antibody conjugates starts from a gentle reduction of the disulfide bridges of the immunoglobulin molecule: in this case, the more sensitive disulfide bridges between the H chains of the antibody molecule are cleaved, while the S—S bonds of the antigen-binding region remain intact, so that practically no reduction of the binding affinity and specificity of the antibody occurs (Biochem. 18, 2226, 1979, Handbook of Experimental Immunology, Vol. 1, Second Edition, Blackwell Scientific Publications, London 1973, Chapter 10). These free sulfhydryl groups of the inter-H-chain regions are then reacted with suitable functional groups of the microparticles at 0° to 37° C., a pH of about 4 to 7, and a reaction period of 3 to 72 hours with formation of a covalent bond, which does not affect the antigen binding region of the antibody. As suitable reactive groups there can be mentioned, for example: haloalkyl, haloacetyl, p-mercuric benzoate, isothiocyanate, thiol, epoxide groups as well as groups, which are to be subjected to a Michael condensation reaction, such as, for example, maleinimides, methacrylo groups (for example, J. Amer. Chem. Soc. 101,3097, 1979).

For linking of the antibody fragments with the microparticles there is in addition a series of suitable bifunctional "linkers" also commercially available (see, for example, Pierce, Handbook and General Catalogue 1986), which are reactive both toward the SH groups of the fragments and toward the amino or hydrazino groups of the microparticles.

As examples there can be mentioned:

m-maleimidobenzoyl-N-hydroxysuccinimide ester (MBS)

m-maleimidobenzoyl-N-sulfosuccinimide ester (sulfo MBS)

N-succinimidyl-[4-(iodoacetyl)-amino]benzoic acid ester (SIAB)

Succinimidyl-4(N-maleimidomethyl)-cyclohexane-1-carboxylic acid (SMCC)

Succinimidyl-4(p-maleimidophenyl)-butyric acid ester (SMPB)

N-succinimidyl-3-(2-pyridyldithio)-propionic acid ester (SDPD)

4-[3-(2,5-dioxo-3-pyrrolinyl)-propionyloxy]-3-oxo- 2,5-diphenyl-2,3-dihydrothiophene-1,1-dioxide acetylalanylleucylalanylamino-p-benzyl acetamido-p-thioureidobenzyl.

Also bonds of noncovalent type can be used for coupling on the biomolecule or macromolecule, and both ionic and van der Waals and hydrogen bridge bonds in alternating portions and strength (lock and key principle) can contribute to the binding (for example, avidin-biotin, antibody-antigen). Also inclusion compounds (host guest) of smaller complexes in larger cavities in the macromolecule are possible.

The coupling principle consists first in producing a bifunctional macromolecule, by either an antibody hybridoma, directed against a tumor antigen being fused with a second antibody hybridoma directed against the microparticles according to the invention or the two antibodies being chemically linked with one another by a linker (for example, in the way indicated in J. Amer. Chem. Soc. 101, 3097 (1979)) or the antibody, directed against the tumor antigen, optionally binding on avidin (or biotin) by a linker [D. J. Hnatowich et al., J. Nucl. Med. 28, 1294 (1987)]. Instead of the antibodies, their corresponding F(ab) or F(ab')$_2$ fragments can be used. For the pharmaceutical use, first the bifunctional macromolecule is injected, which concentrates on the target site, and then periodically the microparticle according to the invention [optionally bound on biotin (or avidin)], which in vivo are coupled on the target site and their diagnostic or therapeutic action can develop there. Further, also other coupling methods can be used such as, for example, the "Reversible Radiolabeling" described in Protein Tailoring Food Med. Uses [Am. Chem. Soc. Symp.] (1985), 349.

With the so-called solid phase coupling a particularly simple method for the production of antibody conjugates or antibody fragment conjugates is available: the antibody is coupled on a stationary phase (e.g., an ion exchanger), which is located, for example, in a glass column. By successive rinsing of the column with a solution suitable for generation of aldehyde groups, washing, rinsing with a solution of the functionalized microparticles, washing and then eluting of the conjugate very high conjugate yields are obtained.

This process allows the automatic and continuous production of any amounts of conjugates.

Other coupling steps can also be performed in this way. Thus fragment conjugates can be produced, for example, by the sequence papain reduction/bifunctional linker/functionalized microparticles.

Then the compounds thus formed are preferably chromatographically purified.

Particles in the size of 0.04–100 microns, preferably 0.1–40 microns, can be produced. The size of the particles can be basically influenced, perhaps with a few routine orientation experiments, by variation of the starting concentration of monomer, surfactant and pH.

Examples for the production of particles of specific size:

| 1) | acrolein concentration: | 10% (w/v) |
|---|---|---|
| | surfactant concentration | 1.5% (w/v) |
| | pH: | 10.0 |
| | temperature: | 4° C. |

If these conditions are selected, particles are obtained with an average diameter of 750 nm.

| 2) | acrolein concentration: | 20% (w/v) |
|---|---|---|
| | surfactant concentration | 0.2 (w/v) |
| | pH: | 10.0 |
| | temperature: | 2° C. |

Under these conditions, particles are obtained with an average diameter of 40 microns.

3) Under the same conditions as under 2) but at a acrolein concentration of 10% (w/v), particles are obtained with an average diameter of 8 microns.

| 4) | acrolein concentration: | 10% (w/v) |
|---|---|---|
| | surfactant concentration | 0.5 (w/v) |
| | pH: | 11.0 |
| | average particle diameter: | 560 nm |

5) Under the same conditions as under 4) but at a pH of 9, an average particle size of 3.2 microns results.

Polyglutaraldehyde sodium hydrogensulfite adduct (PGL) is used as surfactant.

Polyacrolein sodium hydrogensulfite adduct (PAC-SO$_3$) can also be used instead of polyglutaraldehyde sodium hydrogensulfite adduct (PGL) without an effect on the particle size being observed.

Synthesis of PGL

A 25% aqueous solution of glutaraldehyde is purified on activated carbon. Then the solution is freed of O$_2$ by passing N$_2$ in the aqueous solution. Further, a buffer solution (phosphate buffer, 1 molar) is adjusted to pH= 11. The buffer solution is also freed of O$_2$ by passage of N$_2$. The buffer solution and glutaraldehyde solution are brought together and polymerized under N$_2$ atmosphere for 72 hours. Then the polymer is filtered and washed with acetone and water. The washed polymer is dried in the vacuum-drying oven at 45° C. 5 g of polyglutaraldehyde is dissolved in 30 ml of H$_2$O, which contains 12.5 g of NaHSO$_3$. The solution is dialyzed with distilled H$_2$O. Then the solution is freeze-dried.

The particles according to the invention can be suspended in aqueous solutions without aggregation of the particles occurring. For the production of a galenic formulation, which can be administered parenterally, aqueous solutions can be used, which contain isotonizing additives such as sodium chloride, sugar alcohols (mannitol, sorbitol, xylitol, etc.) or sugars (glucose, fructose). For adjustment of the pH, buffers such as trometamol/HCl, citric acid/NaOH, etc. can be selected.

Synthesis of PAC-SO$_3$

A. 100 ml of distilled water is added to a three-neck flask provided with dropping funnel and stirrer and freed of nitrogen by passage of oxygen. Then 1.829 g of K$_2$S$_2$O$_8$ is added and dissolved. After the K$_2$S$_2$O$_8$ has completely dissolved, freshly distilled acrolein is added to this solution. Then 1.14 g of AgNO$_3$, dissolved in 5 ml of water, is added and polymerized for 2 hours with stirring. The precipitated polymer is filtered off, washed several times with water and then, to remove silver ions, 1 liter of water, in which 1.63 g of sodium thiosulfate is dissolved, is resuspended for 1 hour. The polymer is filtered off and dried in a vacuum drying oven at 45° C. The dried polymer is coarsely ground in a mortar. 10 g of ground polymer is dissolved in 100 ml of sodium hydrogensulfite (37%). Then the solution is dialyzed against distilled water (cut off 5000 d). The dialyzate is used as surfactant for the production of polyacrolein microparticles.

B. 100 ml of distilled water is placed in a round-bottom flask. 20 ml of freshly distilled acrolein is added with stirring. Then the pH of the reaction mixture is adjusted to 10.5 by addition of NaOH solution (2N) and it is polymerized for 2 hours with stirring. The precipitated polymer is filtered off, washed several times with water and dried in a vacuum-drying oven at 45° C. 10 g of polymer is dissolved in 100 ml of NaHSO$_3$ solution (37%). The solution is dialyzed against bidistilled water (Cut off 5000 d). The residue is used as surfactant in the production of polyacrolein microparticles.

EXAMPLES

1) In 100 ml of a formulation there are contained:

| particles: | 100 mg |
|---|---|
| trometamol: | 2.4 mg |
| + HCl for pH = 7.4 | |
| mannitol: | 5500 mg |
| water to: | 100 ml |

2) In 100 ml of a formulation there are contained:

| particles: | 50 mg |
|---|---|

| sodium chloride: | 860 mg |
| water to: | 100 ml |

A floating of the particles can be prevented by the average density of the particle being adapted to that of the surrounding vehicle.

This can be achieved by additions of substances of higher density (x-ray contrast media, magnetite). This possibility is offered especially in the case of particles with slight polyaldehyde content.

The pharmaceutical agents according to the invention contain 0.1 µg–100 mg of microparticles/ml, preferably 10 µg–1 mg of microparticles/ml of galenic formulation and are metered as a rule in doses of 0.01 ml–10 ml/kg, preferably 0.1–1 ml/kg of body weight, e.g., for use as ultrasound contrast media. They are intended for enteral and parenteral administration conventionally; for example, for heart imaging, the image is taken immediately after or even during administration of the contrast agent.

For use in hyperthermy therapy the pharmaceutical agents according to the invention as a rule are used in amounts of 0.001–10 mg, preferably 0.01–1 mg per g of tumor.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding German application P 40 04 430.0, are hereby incorporated by reference.

Methods for the production of the contrast medium
1st Reaction step:

A) An aqueous solution containing a surfactant (0.01–5% w/v) is cooled to 0° C. with stirring. At the same time a gas is passed in the solution. The pH of the solution is adjusted with NaOH to the desired value (preferably 9–13). The monomer or monomer mixture is added to this solution. The stirring speed is reduced after 30 minutes. After 1 hour, the reaction mixture is diluted with the above-indicated surfactant-containing aqueous solution. The stirring speed is reduced still more. After 4 hours, the precipitated microparticles, not containing gas, are decanted from the remaining suspension and discarded. The decanted suspension is dialyzed to purify the contrast medium of residual monomers.
Yield: 80–90%

B) An aqueous solution, which contains the desired surfactant and monomer amount, is cooled to 0° C. At the same time, the desired gas is passed through the solution with stirring. Then the pH of the solution is preferably adjusted to 9–13 with NaOH. The, reaction mixture is diluted after 1 hour. After 3–4 hours the suspension containing the microparticles is separated from the precipitated polymer which is discarded. The suspension is purified by dialysis.
Yield: 80–90%

Example 1

91 ml of 0.5% aqueous surfactant solution is put into a flask. The pH of the solution is adjusted to 11 with 0.2N NaOH solution. $N_2$ is passed through the solution. 9.5 ml of freshly distilled acrolein is instilled into the 0.5% surfactant solution cooled to 0° C. Another 100 ml of 0.5% surfactant solution is added to the reaction mixture after 1 hour. After 3 hours the suspension containing the microparticles is decanted from the precipitated polymer and purified by dialysis.

Example 2

82 ml of 0.08% aqueous surfactant solution is put into a flask. The solution is cooled to 0° C. 18 ml of freshly distilled acrolein is added to the cooled solution. Argon is passed in the solution with stirring. After 1 hour, the pH of the solution is adjusted to 12 with 0.2N NaOH solution. After 2 hours 100 ml of 0.08% surfactant solution is added. After 3 hours the solution is decanted and dialyzed.

Example 3

70 ml of 0.08% aqueous surfactant solution, which contains 10% dimethylformamide, is put into a flask. The pH of the solution is adjusted to 11.5 with 0.2N NaOH solution. The solution is cooled to 0° C. At the same time, $N_2$ is passed in the solution. 30 ml freshly distilled acrolein is instilled into this solution. After 1 hour, 100 ml of 0.08% surfactant solution is added to the solution. After 4 hours the suspension is separated from the precipitated polymer and purified.

Example 4

91 mm of 0.5% aqueous surfactant solution, which contains 5% magnetite, is cooled to 0° C. in a flask. The pH of the solution is adjusted to 12 with 0.2N NaOH. $N_2$ is passed through the solution. 9 ml of freshly distilled acrolein is instilled into the solution cooled to 0° C. After 1 hour, 100 ml of the 0.5% surfactant solution is added to the reaction mixture. The suspension containing the microparticles is separated from the precipitated polymers by decanting and dialyzed.

Example 5

91 ml of 0.5% surfactant solution is put into a flask. The pH of the solution is adjusted to 12 by addition of 0.2N NaOH solution. The solution is cooled to 0° C. Argon is passed through the solution. 9 ml of freshly distilled acrolein, which contains 5% butyl cyanoacrylate, is instilled into this solution. After 1 hour another 100 ml of 0.5% surfactant solution is added. The suspension is separated from the sediment and purified.

Example 6

91 ml of 0.08% aqueous surfactant solution is put in a flask. The pH of the solution is adjusted to 10.5 by addition of 0.2N NaOH solution, The solution is cooled to 0° C. $N_2$ is passed through the solution. 9 ml of freshly distilled acrolein, which contains 20% alpha-methylacrolein, is instilled into this solution. After 1 hour, another 100 ml of 0.08% surfactant solution is added. After 2 hours the microsphere suspension is separated from the sediment and purified.

Example 7

91 ml of 0.08% aqueous surfactant solution, which contains 25% isopentane, is put in a flask. The solution is cooled to 0° C. 9 ml of freshly distilled acrolein is added to this solution with stirring. The reaction mixture is filtered after 2 hours. The microparticles are purified by washing with water. The microspheres are resuspended in water.

Surfactant solution: polyglutaraldehyde sodium hydrogensulfite adduct.

2nd Reaction step

A suspension of polyacrolein microparticles in distilled water is adjusted to a pH of 6.5 by addition of 0.01N HCl solution. An excess of the amine-containing ligand is added to this suspension with stirring at room temperature. The pH of this solution is previously adjusted to 8 by addition of 0.01N NaOH solution.

Subsequently, stirring is performed, as a function of the stirring speed, up to 48 hours at room temperature. Dialysis against water is performed to remove the excess amine-containing ligand.

Optionally the formed Schiff bases are reduced to amines by addition of reducing agents.

Example 8

1000 mg of polyacrolein microparticles from example 1 is resuspended in 50 ml of water. 1000 mg of 3-aminopropane-1-sulfonic acid is added to this suspension and stirred at room temperature for 48 hours. Then the suspension is dialyzed against water.

Then it is mixed with 150 mg of $NaBH_3CN$ and stirred for 24 hours at ph 7.5. This suspension is then dialyzed against water.

Optionally the amine can be alkylated or acetylated with chloroacetic acid, acetic anhydride or diglycolic acid anhydride.

Example 9

1000 mg of polyacrolein microparticles from example 2 is resuspended in 50 ml of water. 1000 mg of 3-aminopropane phosphate is added to this suspension and stirred at room temperature for 48 hours. Then the suspension is dialyzed against water.

Then it is mixed with 150 mg of $NaBH_3CN$ and stirred for 24 hours at pH 7.5. This suspension is then dialyzed against water.

Optionally the amine can be alkylated or acetylated with chloroacetic acid, acetic anhydride or diglycolic acid anhydride.

Example 10

1000 mg of polyacrolein microparticles from example 3 is resuspended in 50 ml of water. 1000 mg of 8-aminooctanoic acid is added to this suspension and stirred at room temperature for 24 hours. Then the suspension is dialyzed against water.

Then it is mixed with 150 mg of $NaBH_3CN$ and stirred for 24 hours at pH 7.5. This suspension is then dialyzed against water.

Optionally the amine can be alkylated or acetylated with chloroacetic acid, acetic anhydride or diglycolic acid anhydride.

Example 11

1000 mg of polyacrolein microparticles from example 4 is resuspended in 50 ml of water. 1000 mg of 5-aminovaleric acid is added to this suspension and stirred at room temperature for 36 hours. Then the suspension is dialyzed against water.

Then it is mixed with 150 mg of $NaBH_3CN$ and stirred for 24 hours at pH 7.5. This suspension is then dialyzed against water.

Optionally the amine can be alkylated or acetylated with chloroacetic acid, acetic anhydride or diglycolic acid anhydride.

Example 12

1000 mg of polyacrolein microparticles from example 5 is resuspended in 50 ml of water. 1000 mg of D-glucoseamine hydrochloride is added to this suspension and stirred at room temperature for 30 hours. Then the suspension is dialyzed against water.

Then it is mixed with 150 mg of $NaBH_3CN$ and stirred for 24 hours at pH 7.5. This suspension is then dialyzed against water.

Optionally the amine can be alkylated or acetylated with chloroacetic acid, acetic anhydride or diglycolic acid anhydride.

Example 13

1000 mg of polyacrolein microparticles from example 6 is resuspended in 50 ml of water. 1000 mg of hexamethylenediamine is added to this suspension and stirred at room temperature for 24 hours. Then the suspension is dialyzed against water.

Then it is mixed with 150 mg of $NaBH_3CN$ and stirred for 24 hours at pH 7.5. This suspension is then dialyzed against water, Optionally the amine can be alkylated or acetylated with chloroacetic acid, acetic anhydride or diglycolic acid anhydride.

Example 14

1000 mg of polyacrolein microparticles from example 7 is resuspended in 50 ml of water. 1000 mg of polylysine (MW=32,600 daltons) is added to this suspension and stirred at room temperature for 30 hours. Then the suspension is washed with water.

Example 15

100 mg of polyacrolein microparticles from example 5 is resuspended in 2.5 ml of water. 250 mg of human serum albumin, dissolved in 2.5 ml of water, is added to this suspension and stirred at room temperature for 8 hours. Then the suspension is dialyzed against distilled water (cut off 100,000).

Example 16

1000 mg of polyacrolein microparticles from example 4 is resuspended in 50 ml of water, 1000 mg of (2-diethylamino)-ethylamine is added to this suspension and stirred at room temperature for 20 hours, Then the suspension is dialyzed against water.

Example 17

300 mg of polyacrolein microparticles from example 1 is resuspended in 7.5 ml of distilled water. 750 mg of 3-aminopropane-1-sulfonic acid, dissolved in 7.5 ml water, is added to this suspension and stirred at room temperature for 24 hours. Then the suspension is dialyzed against distilled water (cut off 1000 d).

Example 18

200 mg of polyacrolein microparticles from example 7 is resuspended in 5 ml of distilled water. 500 mg of lysine, dissolved in 5 ml water, is added to this suspension and stirred at room temperature for 24 hours. Then the suspension is dialyzed against distilled water (cut off 5000 d).

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

In vitro tests

In in vitro experiments by backscattering measurements of the echo amplitude of suspensions of microparticles according to the invention, selected as examples, their very good acoustic properties are substantiated.

To explain the in vitro tests and the figures obtained from them:

The measuring device consists of an ultrasonic transmitter combined with an ultrasonic receiver and a measuring cuvette with the specimen. An ultrasonic pulse is sent out to measure the acoustic properties of the specimen. The pulse is scattered on the glass wall of the cuvette, passes through the specimen and then, if the specimen is not echogenic, is scattered on the rear of the cuvette. The backscattering of the ultrasonic pulse is measured by the receiver and indicated by a change of the amplitude (see figures).

Figure 1:
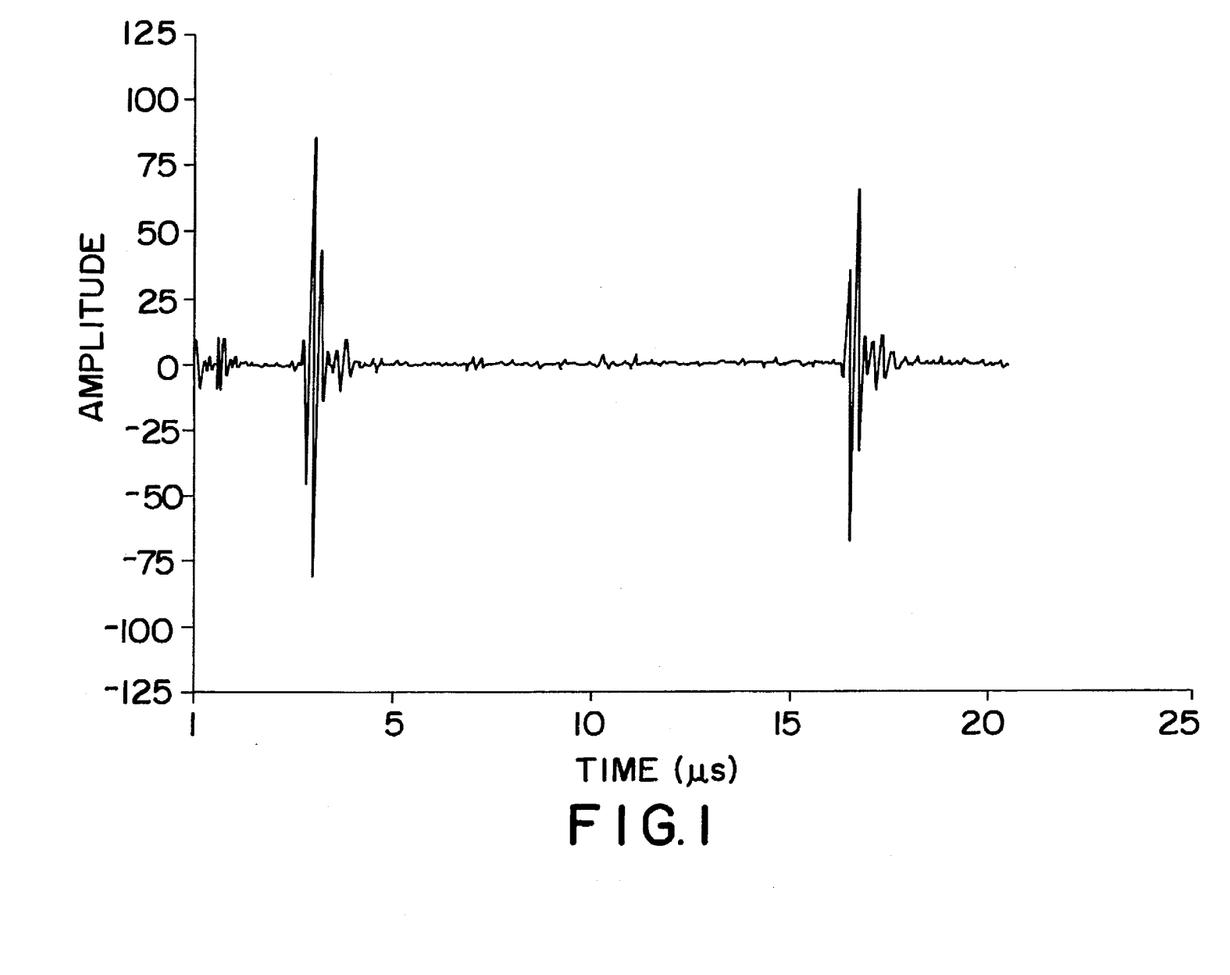

The backscattering behavior of water (as example for the nonechogenic specimen) is represented in FIG. 1. The backscattering amplitude of the front wall (at 3 microseconds) and the back wall (at about 16 microseconds) of the cuvette can be clearly seen.

Figure 2:
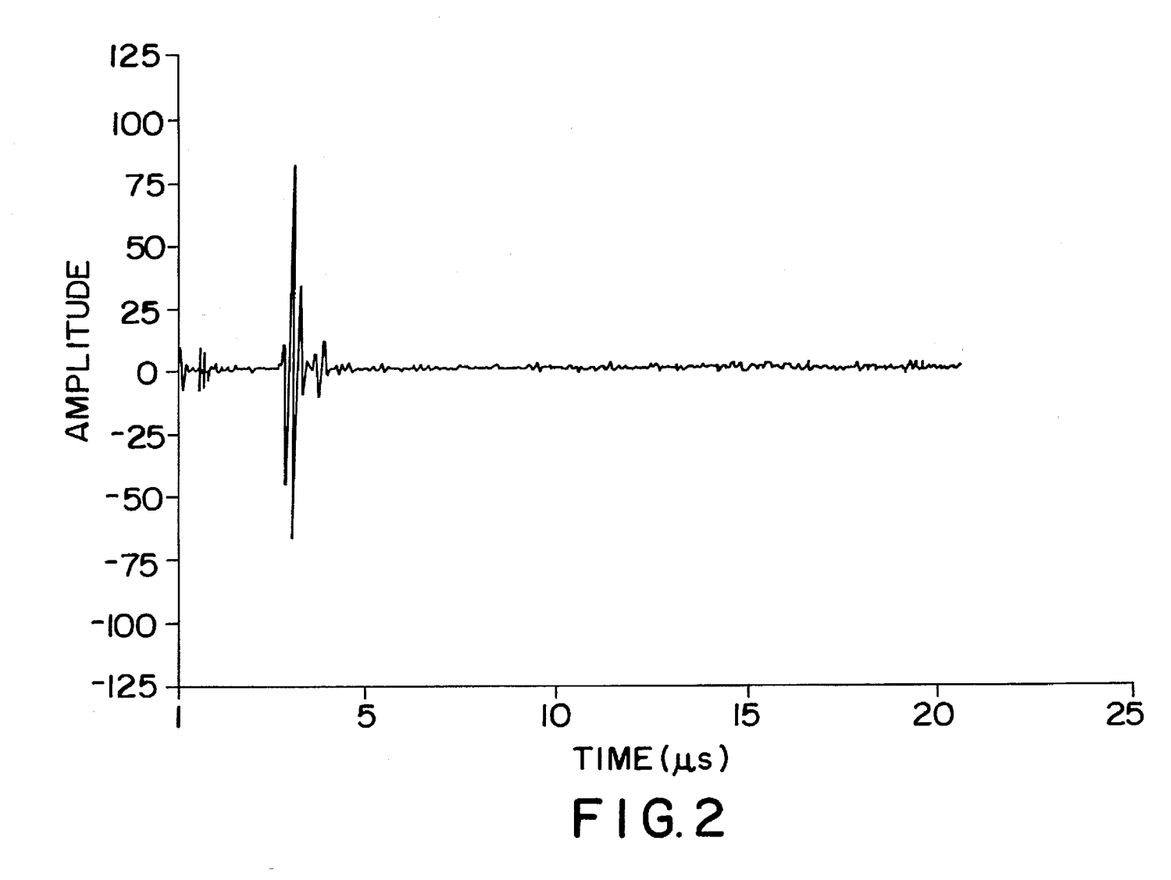
Figure 3:
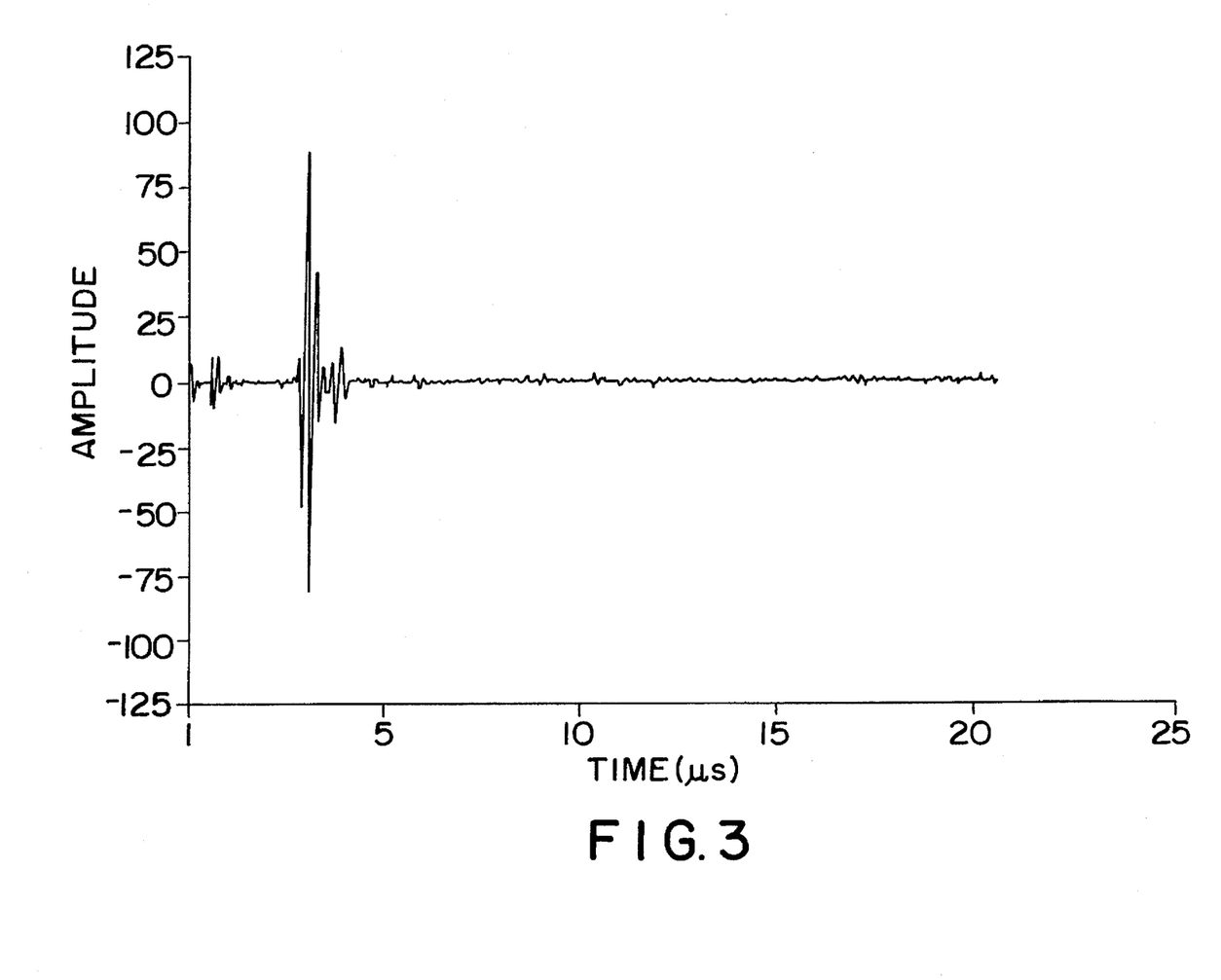
Figure 4:
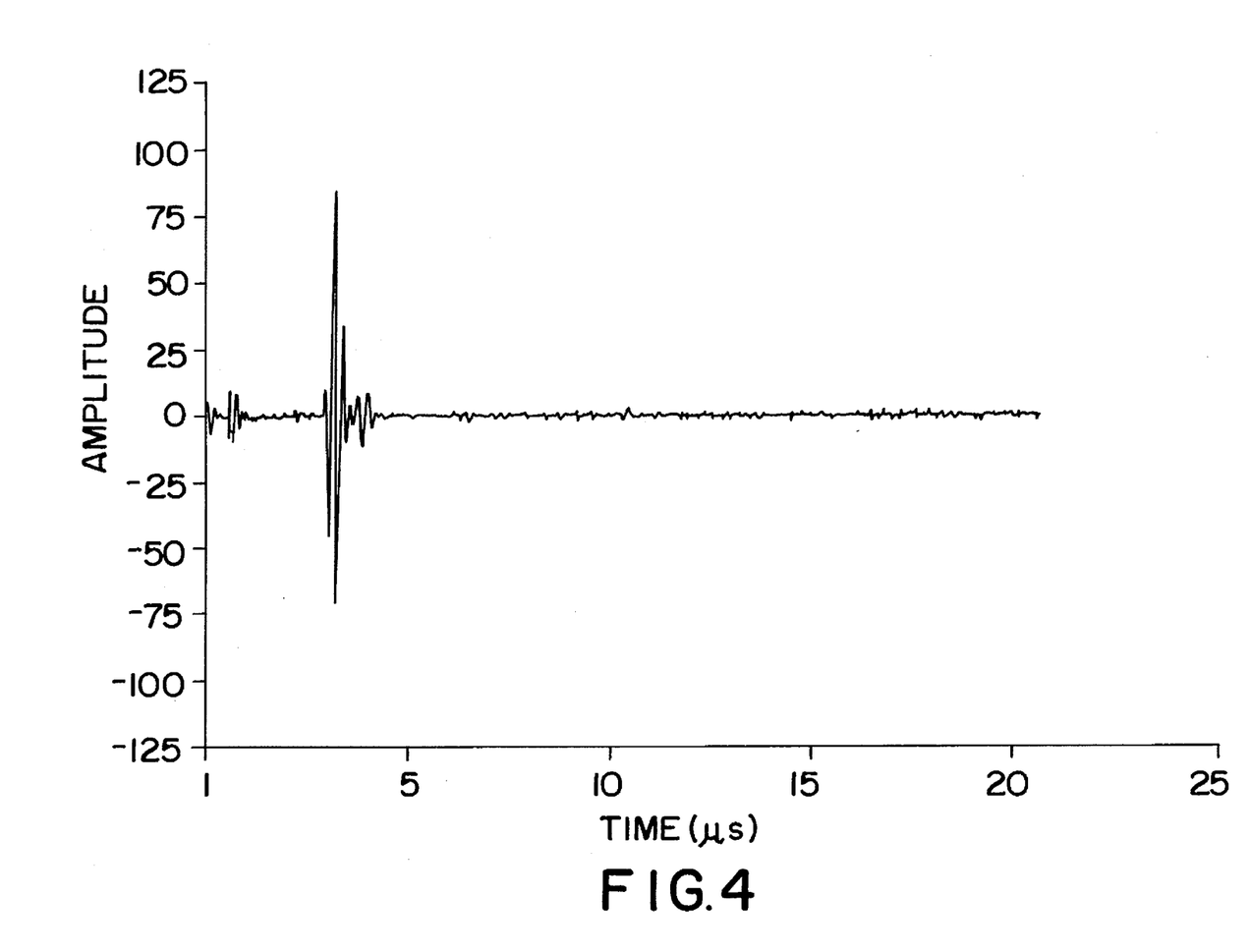

If an echogenic specimen is measured, a backscattering behavior results as reproduced in FIG. 2–4. The backscattering signal of the cuvette wall is not maintained, since the ultrasonic pulse by the interaction with the echogenic specimen is dissipated or so changed that no backscattering to the receiver can any longer take place.

The backscattering amplitudes of aqueous particle suspensions or examples 8 (FIG. 2), 11 (FIG. 3) and 15 (FIG. 4), in a concentration or 0.5 mg/ml each, were determined.

In vivo tests

To perform an echocardiographic examination on a dog (beagle) of about 10 kg, the contrast media according to the invention were used as follows: from the vial with the ready-made suspension 1 ml of the solution is taken, which contains 40 micrograms/ml of particles coupled with albumin (example 15) in 5% glucose solution. The injection of this contrast medium takes place in the vena saphena ramus caudalis by a three-way cock, open all-around, with an injection rate of at least 1 ml/s, but more favorable with a rate of 3 ml/s, followed by a postinjection of 5 ml of a physiologically common salt solution (0.9%). The postinjection takes place to obtain a contrast medium bolus lasting as long as possible. Before the injection an "apical four-chamber view" is put on the test animal with a usual commercial sound head for the echocardiography on the thorax wall (transthoracic lead) and fastened with a clamp.

Before, during and after the injection the sound lead are indicated on the display of the ultrasonic examination device and optionally documented on videotape or with a videoprinter. This test arrangement corresponds to the prior art and is known to one skilled in the art.

With the ultrasonic contrast medium reaching the right heart, the contrast effects can be tracked in color Doppler, in 2D echo image or in M mode echo image. The contrast medium first labels the blood of the right atrium, then the right ventricle and finally the pulmonary artery are contrasted. In this case, a homogeneous filling occurs, which lasts a sufficient time for a diagnostic examination. While the cavities of the right heart are again filled with uncontrasted blood (decrease and disappearance of the echogenity in the heart cavities), the contrast medium appears after the lung passage (transcapillary) in the pulmonary veins, then fills the left atrium, the left ventricle and the subsequent high-pressure system homogeneously. The contrast effects in the cavities of the left heart last longer than those in the right heart side. Besides the contrasting of cavities of the left heart, a contrasting of other organs, which the blood circulation reflects, takes place.

The use of the ultrasonic contrast media according to the invention is not limited to visualization of the blood streams in the vessel system, a contrasting of body cavities is also possible. Caused by, the blood circulation representation the examination of other organs with these contrast media can also take place with good success.

What is claimed is:

1. Microparticles consisting essentially of (a) a biodegradable polymer having a molecular weight of 1–30 Kd, obtainable by polymerizing a polymerizable aldehyde, and (b) 0.01–2 wt % of a gas and/or liquid with a boiling point below 60° C. relative to the amount of polymer, said microparticles having a diameter of 0.1 to 40 µm and said aldehyde having been polymerized in the presence of said gas and/or liquid.

2. Microparticles according to claim 1, wherein the biodegradable polymer is a copolymer comprising a polymerizable aldehyde and a copolymerizable additive.

3. Microparticles according to claim 1 further containing 0–5 wt % of crosslinkers and, wherein the biodegradable polymer is crosslinked.

4. Microparticles according to claim 1, wherein a bio- or macromolecule is bound to said polymer.

5. Microparticles according to claim 4 further containing 1–95 wt % of a coupling agent based on the amount of polyaldehyde, and, wherein the bio- or macromolecule is bound to the polymer via said coupling agent.

6. Microparticles according to claim 1, wherein said biodegradable polymer contains 0.01–1 wt % relative to the weight of said polyaldehyde of a surfactant or a mixture of surfactants.

7. Microparticles according to claim 1, wherein the polymerizable aldehyde monomer is an alpha,beta-unsaturated aldehyde, an alpha-substituted acrolein derivative, and/or a dialdehyde.

8. Microparticles according to claim 7, wherein the α-substituted acrolein derivative is α-methylacrolein, α-chloroacrolein, α-phenylacrolein, α-ethylacrolein, α-isopropylacrolein, α-n-butylacrolein, or α-n-propylacrolein.

9. Microparticles according to claim 7, wherein the dialdehyde is glutaraldehyde, succinaldehyde, or a derivative thereof.

10. Microparticles according to claim 2, wherein the additive capable of copolymerization is α-substituted acrolein, β-substituted acrolein, ethyl cyanoacrylate, methyl cyanoacrylate, butyl cyanoacrylate, hexyl cyanoacrylate, methyl methacrylate, a vinyl alcohol, an acrylic acid, a methacrylic acid, an acrylic acid chloride, a methacrylic acid chloride, acrylonitrile, methacrylonitrile, an acrylamide, a substituted acrylamide, an hydroxy methyl methacrylate, mesityl oxide, a dimethylaminoethylmethacrylate-2-vinylpyridine, and/or N-vinyl-2-pyrrolidinone.

11. A process for the production of microparticles according to claim 1, consisting essentially of:

reacting, with mixing, the desired polymerizable aldehyde(s), with an aqueous solution saturated with the desired gas and/or containing the desired liquid with a boiling point below 60° C., at a temperature of −5° C. to +80° C. and a pH of 7 to 14, within 1 minute to 24 hours, wherein the concentration of the aldehyde relative to the reaction mixture is 0.1 to 50 w/v;

after the polymerization has finished, separating particles containing said gas or liquid below 60° C. from particles not containing said gas or liquid; and optionally, purifying the particles containing said gas or liquid below 60° C.

12. A process for the production of microparticles according to claim 11, further comprising:

reacting the microparticles thus obtained with an aqueous solution which contains, relative to the mount of aldehyde, up to an equimolar amount of a coupling agent, with stirring, for up to 3 days, at temperatures of 0° C. to 60° C., and a pH of 3 to 9, and binding a bio- or macromolecule to the resultant microparticles.

13. A process for the production of microparticles according to claim 12, further comprising binding a bio- or macromolecule to the resultant microparticles.

14. A process for the production of microparticles according to claim 11, wherein the polymerizable aldehyde reactant contains a crosslinking agent in a concentration of up to 20% w/v.

15. A process for the production of microparticles according to claim 11, wherein the polymerizable aldehyde reactant contains a crosslinking agent in a concentration of up to 5 % w/v.

16. A process for the production of microparticles according to claim 11, wherein the reaction mixture contains a surfactant in a concentration of from 0.01 to 10% w/v.

17. A process for the production of microparticles according to claim 11, wherein the desired gas is passed through the reaction mixture.

18. Microparticles according to claim 7, wherein the α,β-unsaturated aldehyde is acrolein, crotonaldehyde, or propynoicaldehyde.

19. A pharmaceutical composition comprising microparticles according to claim 1 and a pharmaceutically acceptable adjuvant.

20. A method of obtaining an ultrasonic image comprising administering to a patient microparticles of claim 1 and taking an ultrasonic image of the patient.

21. Microparticles of claim 2, wherein the surfactant is polyethylene oxide; a carboxylic acid salt; a polyoxyethylene fatty acid ester; sodium dioctyl sulfosuccinate; polyglutaraldehyde sodium hydrogen sulfite adduct; polyethylene glycol, a polyoxyethylene polyoxypropylene, sodium oleate, or polyoxyethylene stearate.

22. Microparticles of claim 1, wherein the gas or highly volatile liquid is ammonia, air, helium, neon, argon, xenon, krypton, a sulfur halide, sulfur hexalfluoride, nitrogen, carbon oxides, oxygen, hydrogen, methane, ethane, propane, butane, pentane, neopentane, isopentane, cyclopentane, ethylene, propylene, acetylene, 3,3-dimethyl-1-butyne, 2,3-pentadiene, 2-methyl-2-butene, 2-methyl-1,3-butadiene, 2-butyne, 2-methyl-1-butene, 3-methyl-1-butene, methylene chloride, 1,1-dichloroethylene, isopropyl chloride, dibromodifluoromethane, bromomethane, dimethyl ether, diethyl ether, a fluorinated ether, dimethylaminoacetone, propylene oxide, N-ethylmethylamine, N-ethyldimethylamine, and/or furan.

23. Microparticles of claim 5, wherein said coupling agent is hydroxylamine, butylamine, allylamine, ethanolamine, trishydroxymethylaminomethane, 3-amino-1-propanesulfonic acid, 5-aminovaleric acid, 8-aminooctanoic acid, D-glucosamine hydrochloride, aminogalactose, aminosorbitol, aminomannitol, diethylaminoethylamine, an aniline, sulfonyl acid amide, choline, N-methylglucamine, piperazine, 1,6-hexanediamine, urea, hydrazine, glycine, alanine, lysine, serine, valine, leucine, a peptide, a protein, albumin, human serum albumin, polylysine, gelatin, a polyglycolamine, an aminopolyalcohol, a dextran sulfate with amino groups, N-aminopolyethylene glycol (HO-PEG-NH$_2$), N,N"-diaminopolyethylene glycol (NH$_2$-PEG-NH$_2$), an antibody, an immunoglobulin, PEG linker asparaginic acid, PEG linker glutaminic acid, PEG linker DTPA, PEG linker EDTA, 1,3-propanediol, glycerol, or pentaerythritol.

24. Microparticles of claim 1, wherein said biomolecule is a monoclonal antibody.

25. A pharmaceutical composition according to claim 19, wherein the concentration of microparticles is 1 microgram to 100 mg per ml the composition.

* * * * *